United States Patent [19]

Luceri et al.

[11] Patent Number: 4,518,451
[45] Date of Patent: May 21, 1985

[54] EMBOSSED PANTY LINER

[75] Inventors: Thomas J. Luceri, Little Ferry; Kenneth J. Molee, Hightstown, both of N.J.

[73] Assignee: Personal Products Company, Milltown, N.J.

[21] Appl. No.: 414,104

[22] Filed: Sep. 2, 1982

[51] Int. Cl.³ .................. A61F 13/16; A61F 13/18; B31F 1/20; B32B 31/22
[52] U.S. Cl. .................................. 156/202; 156/209; 156/216; 156/221; 156/226; 156/260; 604/378
[58] Field of Search .............. 156/209, 211, 213, 217, 156/220, 221, 223, 226, 227, 259, 260, 264, 271, 202, 204, 216; 264/146, 284, 293, 500; 604/385, 387, 389; 428/165, 177, 189, 190, 191

[56] References Cited

U.S. PATENT DOCUMENTS

| 1,794,674 | 3/1931 | Cumfer | 156/260 |
| 3,746,592 | 7/1973 | Nystrand et al. | 156/227 X |
| 3,861,974 | 1/1975 | Trombly et al. | 156/226 X |
| 3,881,490 | 5/1975 | Whitehead et al. | 604/387 X |
| 4,023,570 | 5/1977 | Chinai et al. | 604/387 X |
| 4,079,739 | 3/1978 | Whitehead | 604/387 X |
| 4,347,092 | 8/1982 | Hlaban et al. | 156/221 X |

Primary Examiner—Edward Kimlin
Assistant Examiner—Ramon R. Hoch
Attorney, Agent, or Firm—Jason Lipow

[57] ABSTRACT

A thin absorbent undergarment liner is provided which exhibits a clear, aesthetically pleasing embossed pattern on the body facing surface thereof while still maintaining the longitudinal edges soft and comfortable. The liner is provided to have areas of deep depressions on the body facing surface and shallow impressions on the longitudinal edges.

4 Claims, 5 Drawing Figures

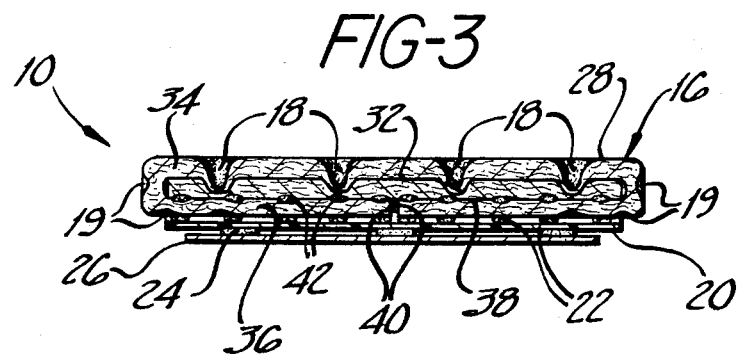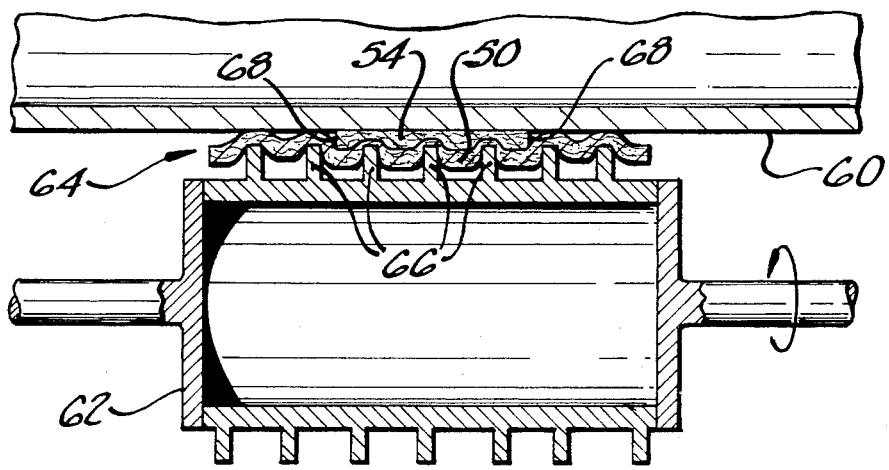

EMBOSSED PANTY LINER

BACKGROUND OF THE INVENTION

This invention relates to protective absorbent liners for undergarments and in particular, the thin absorbent liners intended to fit within the crotch portion of an undergarment and protect the garment from body exudates. Such products are designed to provide such protection between menstrual periods as well as during light flow days and may also be worn during a menstrual period in conjunction with internal sanitary protection products such as catamenial tampons.

Such thin products are now on the market and have met with some commercial success. In an attempt to make the products aesthetically as well as functionally appealing, manufacturers have embossed or otherwise imposed patterns of depressed areas onto the surfaces of the liners, in such patterns as flowers, lines, spots, and the like. Unfortunately, manufacturers have encountered certain problems in attempting to produce thin embossed products manufactured at the high speeds required to commercially provide an inexpensive disposable product such as those being considered herein. To be aesthetically effective, such embossing must be relatively deep; i.e., the depressed areas must be permanently depressed to a degree which represents a major portion of the thickness of the product. Shallow embossing is not visually effective. Unfortunately, the effect of such extreme compression is to produce a rather dense, harsh, inflexible material. While such characteristics are not particularly detrimental when existing on the central portion of the body facing side of a liner, they are a source of discomfort and so undesirable at portions where they are likely to cause chaffing as, for example, at the longitudinal edges of the product i.e., where the product may chafe the thighs of the wearer.

The imperative to manufacture these products at high speed does not allow for careful registration of the embossed pattern on only those areas where they are not detrimental to comfort. Accordingly, heretofore, the choice has been to either emboss the entire product, including the longitudinal edges, with the same depth of depressed areas thereby producing a product which manifests itself in user discomfort or to reduce the depth of the depressions on the entire product thereby rendering the product less visually appealing.

SUMMARY OF THE INVENTION

In accordance with the teachings of this invention a product is provided and a method is described which obviate the shortcomings described above in connection with thin absorbent liners. Specifically, the product and methods of this invention result in a liner which exhibits a clear, aesthetically pleasing pattern on the body facing surface of the napkin while still maintaining the longitudinal edges soft and comfortable. This product may be manufactured by the method of this invention at high speeds without the need for careful registration of the embossing equipment or any other processing steps which will necessarily retard rapid production.

The thin, protective absorbent liner for undergarments taught herein comprises a sheet of absorbent material having a longitudinal direction and a transverse direction. A planar absorbent insert is positioned with its first major surface overlying a central portion of the sheet, with the sheet extending on either side of the insert. These side extensions of the sheet are folded onto the second major surface of the insert to form a multiplied absorbent body for the liner, with the central portion of the sheet constituting the body facing side of the liner, the side extensions constituting the garment facing side of the liner and the folded edges between the side extensions and the central portion constituting the longitudinal edges of the liner.

In accordance with the teachings of the invention the body facing side of the absorbent body has imposed therein a pattern of relatively deep depressed areas whereas, the longitudinal edges have imposed therein a pattern of relatively shallow depressed areas. Thus, the deep depressions on the body facing side provide clear, visually perceptable definition to the patterns while in no way contributing to user discomfort. On the otherhand, the shallow depression on the longitudinal edges are densified to an insufficient degree to create the discomfort heretofore associated with embossed liners.

In a preferred embodiment, the side extensions are held in place on the second major surface of the insert by adhesive means such as lines, spots, or the like of adhesive material deposited at the interface between the side extensions and insert. Further, in a preferred embodiment, the garment facing side of the absorbent body is provided with a fluid impervious cover to protect the undergarment from staining. Such cover may comprise a thin film of polyethylene or an equivalent fluid barrier means. The liner may also include a pressure-sensitive adhesive layer on its garment facing side for attachment to the crotch portion of the wearer's undergarment.

In accordance with the teachings herein the liner of this invention, and specifically, the embossed absorbent body for such liner, may be manufactured by passing an elongated sheet of absorbent material having a first and second major surface to an assembly line. A planar, absorbent insert having first and second major surfaces is superimposed upon a central longitudinal portion of the first major surface of the sheet, the first surface of said absorbent insert being in face-to-face contact with the first surface of the sheet and, with the insert being narrower than said sheet, the sheet extending therefor on either side of said insert. A pattern of depressed areas is then imposed onto the second major surface of the sheet, the pattern extending transversely beyond the insert and onto the side extensions of the sheet with the depressed areas being deeper in the portion of the sheet overlaid by the insert, relative to the depressed areas in the remaining portions of the second major surface of the sheet. The side extensions of the sheet are then folded onto the second major surface of the insert to form the absorbent body for the liner. In a preferred embodiment, a fluid impervious barrier film is adhered to the folded side extensions which will correspond to the garment facing side of the finished liner.

BRIEF DESCRIPTION OF THE DRAWINGS

The invention will be better understood by consideration of the following description, taken together with the appended drawings in which:

FIG. 3 is a transverse, cross-sectional view of the liner of FIG. 1, taken through line 3—3 of FIG. 1;

FIG. 5 is a cross-sectional view taken through the embossing station along line 5—5 of FIG. 4.

DETAILED DESCRIPTION OF THE INVENTION

Figure 1:
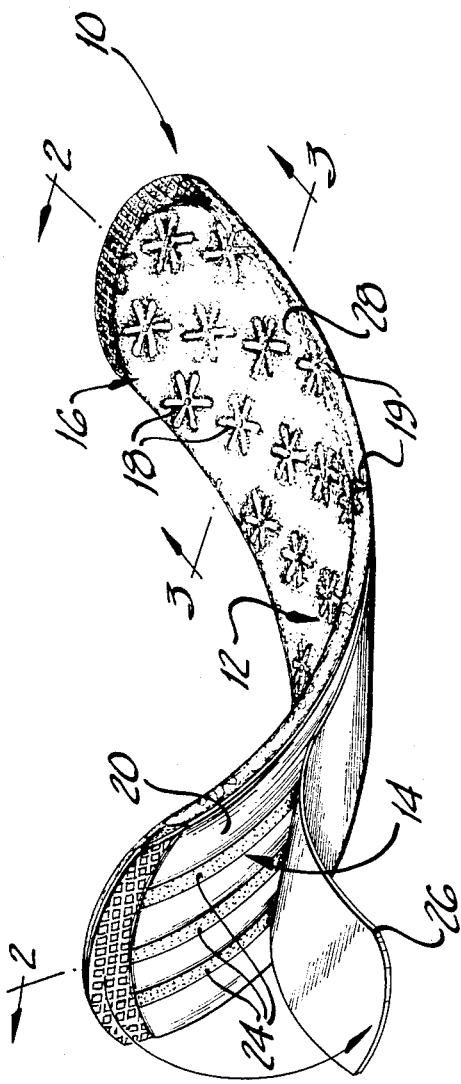
FIG. 1 is a perspective view of the absorbent undergarment liner of this invention being illustrated out of planar configuration to show both major surfaces and having its protective strip partially peeled from the garment side of the liner.
Figure 2:
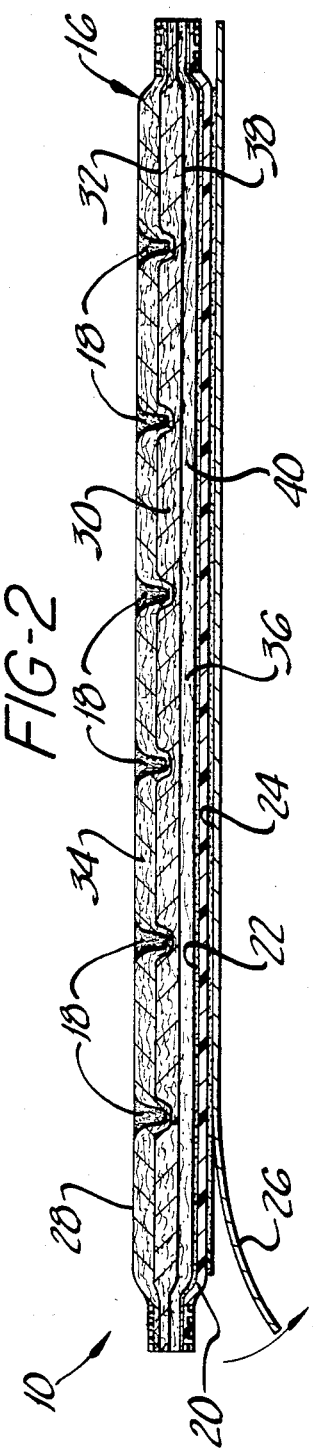
FIG. 2 is a longitudinal, cross-sectional view of the liner of FIG. 1 taken through lines 2—2 of FIG. 1.

FIGS. 1-3 illustrate, in perspective, longitudinal cross-sectional and transverse cross-sectional views, respectively, a liner 10 embodying the teachings of this invention. The liner 10 comprises a body facing, body fluid pervious side 12 and a garment facing, body fluid impervious side 14. The body facing side of the liner consists of a multiplied absorbent body 16 having embossed on its body facing surface, a pattern of depressed areas 18. As illustrated in FIG. 1, the pattern is in the form of a stylized snowflake design and is intended to add aesthetic value to the liner. It will be clear that any pattern may be freely substituted for the snowflake pattern illustrated in this specific embodiment and that the advantages of the invention, as hereinafter set out and described, will equally pertain. For example, the pattern may take the form of various geometric shaped such as circles, diamonds, squares, curves or lines or such other stylized figures such as flowers, stars or the like.

Affixed to the garment facing side of the absorbent body 16 is a layer of body fluid impervious material 20 provided to act as a barrier to body fluids and prevent the "strike through" of such fluids onto the undergarment of the wearer. This layer may comprise any thin flexible body fluid impermeable material such as, for example, a polymeric film, e.g., polyethylene, polypropylene, cellophane or even a normally fluid pervious material that has been treated to be impervious such as impregnated fluid repellant paper. As is illustrated in the drawings, the body fluid impervious layer 20 is affixed to the absorbent body 16 by means of a plurality of longitudinally extending lines of adhesive 22.

Disposed on the garment facing surface of the impervious layer 20 are longitudinally extending pressure-sensitive adhesive means 24, provided for attaching the liner to the crotch portion of an undergarment. While such adhesive means are illustrated in the form of longitudinally extending lines, it will be understood that various patterns such as spots, or transverse lines will be suitable. The adhesive employed may be any of the large number of pressure-sensitive adhesives available on the market, including for example, the water based pressure-sensitive sensitive adhesives such as the acrylate adhesives e.g., vinyl acetate-2 ethyl hexyl acetate copolymer which is generally combined with tackifiers such as ethylene amine. Alternatively, the adhesive may comprise the rapid-setting thermoplastic (hot melt) adhesives such as block copolymers exemplified by the A-B-A block copolymers wherein the A end block is polystyrene and the midblock is polyolefin copolymer such as poly (ethylene) poly(butylene)copolymer. The adhesive element may also comprise a double faced tape.

Overlying the adhesive elements 24 is a protective release strip 26 which is provided to protect the adhesive elements 24 from dirt and unintended adhesion prior to use. The strip 26 may be constructed of any suitable sheet-like material which adheres with sufficient tenacity to the adhesive element to remain in place prior to use but which can be readily removed when the liner is to be used. A particularly useful material is a semibleached kraft paper, the adhesive contacting side of which has been silicone treated to provide easy release from the adhesive elements 24.

In accordance with this invention the absorbent body 16 comprises a sheet 28 of absorbent material folded about a centrally located planar insert 30 of absorbent material. The insert has a first major surface 32 which is in face-to-face contact with a longitudinally extending (with respect to the finished liner) central portion 34 of the sheet 28. The sheet 28 extends on either side of the insert 30 and the side extensions 36 are folded into face-to-face contact with the second major surface 38 of the insert. Accordingly, as best viewed in transverse cross-section such as is shown in FIG. 3, the sheet 28 is in a C-form configuration, enfolded about the insert 30 to form the multi-plied absorbent body 16 with the central portion 34 of the sheet forming the body facing side of the absorbent body, the side extensions 36 forming the garment facing side of the absorbent body and the folds between the central portion 34 and the side extension 36 forming the longitudinal edges of the absorbent body. It should be understood that while the extreme longitudinal edges 40 of sheet 28 are shown spaced apart for the purpose of illustration in FIG. 3, these edges may also abutt, substantially closing the "C"-form. The side extensions are held in place adjacent the insert 30 by adhesive means 42.

As is taught herein, the body side of the absorbent body 16 and specifically the central portion 34 of the sheet 28, is provided with a pattern of deep depressions 18 for aesthetic purposes. These depressions must be sufficiently deep to provide clear visual definition of the pattern, and hence extend to a depth which represents a substantial portion of the original thickness of the sheet material and even into the insert. Preferably, for the thin products involved herein, these depressions extend to a depth of at least 70% of the original uncompressed thickness of the sheet material and still more preferably at least 90%. Because of the presence of the insert it will be appreciated that the depressed areas 18 may, in fact, extend to a depth greater than the thickness of the uncompressed sheet and depths of as much as 500%, based on the uncompressed thickness of the sheet are suitable for producing a clear, aesthetically pleasing pattern on the central body facing side of the liner.

In contrast thereto, the depressed areas 19 on the remainder of the sheet 28 i.e., on the longitudinal edges and garment facing side of absorbent body 16, are shallow and extend to a depth which is only a fraction of the depth of the body facing side depressions 18. Preferably the depressions 19, on the remainder of the product are less than 75% of the depth of the depression 18, still more preferably less than 50%.

The absorbent sheet of this invention may comprise any of the absorbent, flexible materials now used for producing body fluid absorbing products. Such sheet should have structural integrity and be capable of having an embossing pattern permanently imposed thereon. The sheet should therefor have a minimum thickness of about 0.01 cm. and preferably at least 0.05 cm. thick. The insert should likewise be constructed of one of such absorbent materials for absorbing body fluids and may in fact be the same material as that of the sheet. The insert must have sufficient thickness so as to allow for the imposition of deep depressions on the body facing side of the absorbent body as compared to the shallow depressions on the remainder of the product. Accordingly, the insert should have a thickness of at least 0.01 cm and preferably 0.25 cms. In general, it is desired that the products of this invention be relatively thin overall and so, preferably the overall thickness of the absorbent body should vary between about 0.125 cm to about 2.0 cm and preferably from about 0.2 to about 1.0 cm.

The choice of materials for the absorbent sheet and insert may vary widely provided, of course, that they conform to the above set out criteria. The materials recited in U.S. Pat. No. 4,023,571 issued May 17, 1977 to J. M. Comerford, et al. and in U.S. Pat. No. 4,023,570 issued on that same day to K. Chinai, et al. may be suitable. As described in these patents, a particularly useful material is the lofty and soft nonwoven, through bonded fabric described in U.S. Pat. No. 3,663,238 issued on May 16, 1972 to G. J. Liloia, et al. This fabric consists essentially of a mixture of approximately 25%, by weight, of long (about 2.9 cms.) rayon fibers and about 75% by weight of short (about 0.2 cm) wood pulp fibers and has a water dispersible binder applied throughout in an amount of between about 1% and about 30% of the weight of the fibers on a dry basis. The binders of choice are the self-curing acrylic latex type, the urethane type or other similar binders. The fabric has a weight of less than about 8 ounces per square yard and a density of about 0.15 to about 0.05 gm per cc.

Another particularly suitable absorbent material for use as both the absorbent sheet and the insert of this invention is a low density, highly absorbent, thermal bonded nonwoven fabric comprising a mixture of absorbent fibers and staple length polyester/polyethylene conjugate fibers. The absorbent fibers are preferably wood pulp or other cellulosic fibers which may have been treated to enhance absorbency. The conjugate fibers are fibers which comprise a polyester core surrounded by a sheath of polyethylene.

Preferably, the conjugate fibers employ high density polyethylene, that is, linear polyethylene that has a density of at least 0.94, and a Melt Index (as determined by ASTMD-1238E method, employing the parameters of 190° C. and 2160 gm) of greater than 1, preferably greater than about 10, and more preferably from about 20 to about 50. The fibers may comprise from about 40 to 60 percent, by weight polyester and preferably from 45 to 55 weight percent polyester, the remainder being polyethylene. Such fibers may be used in deniers of from 1 to about 6 and may be from about ½ inch to about 3 or 4 inches long. Preferably the fabric comprise outer layers of heat fusible fibers having the mixture of wood pulp and conjugate fibers sandwiched therebetween. Such outer layers may consist of the conjugate fibers or may in fact be any heat-fusible materials such as polypropylene fibers, for example. The fabric is stabilized by applying heat thereto under essentially zero pressure whereby thermal bonding takes place without destroying the integrity of the fibers and low density is maintained. Typically, the bulk density of such fabrics is less than about 0.15 grams per cubic centimeter.

Figure 4:
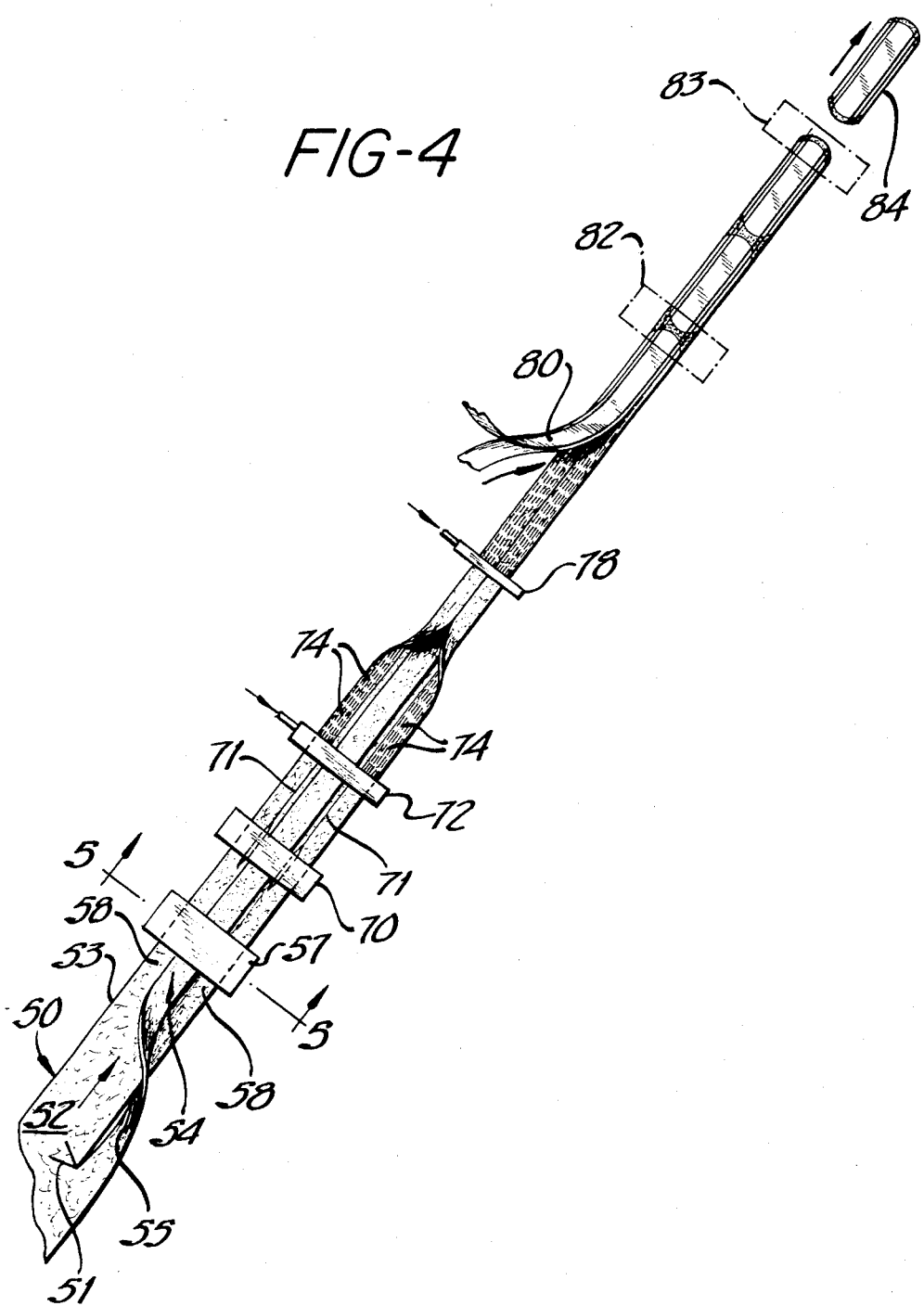
FIG. 4 is a schematic diagram of a process for manufacturing the liner of the invention.

Referring now to FIG. 4, illustrated therein is a schematic assembly line for producing the product of this invention. As is illustrated, an elongated absorbent sheet 50 comprising absorbent material and having a first major surface 52 and an opposed second major surface 53, is passed to the assembly line. Preferably, the sheet 50 is first passed to a slitter 51 wherein a lateral portion thereof is slit from the sheet to form an elongated absorbent insert 54 having a first major surface 55 and a second major surface. It will be understood that insert 54 need not be slit from the sheet 50 but instead may be provided from a wholly independent supply and may be of an entirely different material from that of sheet 50.

The insert is next superimposed upon a central longitudinal portion of the first major surface 52 of the elongated sheet 50 so that this first major surface 52 of sheet 50 is in face-to-face relationship with the first major surface 55 of the insert. The absorbent sheet 50, being wider than the insert, extends on either side of the insert in side extensions 58. The sheet 50, with the superimposed insert 54 is next passed to an embossing station 57 where a pattern of depressions is imposed on the second major surface 53 of sheet 50. The embossing station may comprise two rollers forming a nip therebetween through which the superimposed sheet passes. In such case, the roller overlying the insert is smooth and acts as the anvil roller and the roller pressing against the second major surface 53 of the sheet 50 is provided with a raised pattern and acts to impose the desired pattern of depressions.

The means required to impose the pattern permanently is essentially a function of the choice of absorbent material employed as the sheet and/or the insert. For example, if the materials of construction for these elements is chosen to be the thermal bonded material described above, one or both of the rolls may be heated to a moderate temperature e.g. from about 90° C. to about 125° C., and a permanent "set" will result. On the other hand, if an adhesive bonded fabric such as the above described fabric of the Liloia patent is employed, a permanent set may be achieved by first water conditioning the sheet material so as to increase its moisture content and then imposing the pattern by use of such pressure means as rollers, which are preferably heated. As is well known in the art, the combination of water and pressure, abetted by the application of heat, forms hydrogen bonds among the cellulose molecules making up the absorbent material of the embossed fabric and fixes the fibers into the embossed configuration.

As has been described above and in accordance with the teachings of this invention, it is important that the pattern of depressions be imposed on the sheet 50 after it has been superimposed with the insert 54. In this way, it is possible to easily produce the unique absorbent body of this invention i.e. one which has a pattern of deep depressions on the body side and shallow depressions elsewhere. This aspect of the invention is best illustrated in FIG. 5 which is a schematic, transverse, cross-sectional view through the embossing station of the assembly line shown in FIG. 4. Shown therein, is a smooth anvil roller 60, an embossing roller 62 having raised areas 66, and a nip 64 therebetween. The two rollers are adjustably spring loaded so as to urge them together and close the nip 64. Positioned within the nip is the sheet 50, superimposed by the insert 54. It should be noted that the raised areas 66 extend transversely beyond the edges 68 of the insert thereby insuring that even with substantial misalignment of the insert from the center of the sheet, the sheet will still be completely embossed on that central portion on which the insert lies. By virtue of spring loading, the two rollers are urged together until resisted by the compression limits of the material therebetween and because of the additional presence of the insert, it can be seen that the compression limit will occur in the area where the insert is present and not on either side thereof. Said in other words, the rollers will be spaced apart, in the area of the insert, a distance which will correspond to the resistance to compressive forces of the material therebetween so that the material in this area will be compressed to its limiting value whereas the material on either side of the insert will not reach its limiting value. Accordingly, the depths of depressions found in the area superimposed by the insert will be substantially greater than on either side thereof. Advantageously, it can be seen that the depths of depressions in the superimposed area may even exceed the original thickness of the sheet 50 whereas this is clearly impossible in the areas on either side thereof. It should be noted that the method of this invention provides for self registration of the deep embossing pattern i.e., insuring deep depressions only in the required area and only shallow depressions elsewhere, thereby allowing for the rapid and facile manufacture of the products of this invention.

Referring again to FIG. 4, the now embossed assembly is passed to a scoring station 70 where two score lines 71 are imposed on the first major surface 52 of sheet 50 to facilitate the subsequent folding process. The scored assembly is next passed to an adhesive applicator 72 where adhesive lines 74 are applied to hold the subsequently folded product in place. Thereafter, the side extensions 58 are enfolded about the insert 54 and then, at a second adhesive applicator 78, adhesive is applied for adhering the barrier sheet to the folded side extensions which will constitute the garment facing side of the absorbent body of the finished liner. The assembly is next joined with sub assembly 80 which comprises an elongated sheet of barrier material, pressure-sensitive adhesive for adhering the finished product to the undergarment and the protective release strip, all of which having been described in connection with FIGS. 1-3. Subassembly 80 is adhered to the assembly and pressed thereon. Finally the assembly is passed to a crimping station 82 where the assembly is crimped at intermittent positions corresponding to the ends of the finished liner to close these ends and the product is next cut at a cutting station 83 and separated into the individual liners 84.

While it will be understood that a wide variation of materials, dimensions, and operating parameters are suitable for use within the broad teachings of this invention, a highly satisfactory product is produced by employing for both the sheet and the insert material a thermal bonded absorbent fabric comprising, overall, 54% by weight of wood pulp fibers and 46% by weight of conjugate fibers having a polyester core and a high density polyethylene sheath. The conjugate fibers have a staple length of 3.81 cm. and a denier of 3.0. The materials are so distributed as to provide a pulp/conjugate fiber mixture sandwiched between two veneers of conjugate fibers, the veneers having basis weights of 0.27 oz/yds$^2$ and 0.37 oz/yd$^2$, the heavier veneer ultimately being employed on the body facing side of the product. The fabric is stabilized by passing hot air through the fibers and thereby melting the high density polyethylene which bonds the fibers together upon cooling. The overall fabric has a basis weight of 2.5 oz/yd$^2$, is about 0.165 cm. thick and has machine direction and cross direction tensile strength of 5.3 and 1.1 pounds/inch of width, respectively. The fabric is capable of holding about 17 times its own weight of distilled water.

The sheet material made for the above fabric has a width of 10.48 cm. and the insert, slit from an originally wider sheet of 15.11 cm., has a width of 4.63 cm.

The assembly of sheet and insert are embossed in accordance with the above described method using an embossing roller imposing a snowflake pattern such as is illustrated in FIGS. 1-3. The pattern of the embossing roller is 6.99 cm. wide as contrasted with the 4.64 cm. wide insert. The embossing is carried out using an embossing roller surface temperature of from 93°-121° C., a set gap between anvil and embossing rollers of 0.0025 cm. and an embossing pressure of more than 500 lbs/linear inch of nip.

The finished liner has an overall length of 15.24 cm., and overall width of 5.08 cm. and has the general configuration of that illustrated in FIG. 1-3. The barrier sheet employed is 4.62 cm. wide and comprises a 2 mil. thick polyethylene film. Three longitudinal extending lines of pressure-sensitive, hot melt adhesive are applied to the barrier for adhering the liner to an undergarment. Each of the lines measure 12.7 cm. long by 0.64 cm. wide and is covered by a silicone treated release paper.

We claim:

1. A method for manufacturing an embossed absorbent body for an absorbent liner for undergarments comprising:
    passing an elongated sheet of absorbent material having a first and a second major surface to an assembly line;
    superimposing, on a central, longitudinal portion of the first major surface of said elongated sheet, the first major surface of an absorbent insert with said sheet extending tranversely on either longitudinal side of said insert;
    imposing onto the second major surface of said sheet, a pattern of depressed area, said pattern extending transversely beyond said insert and onto said side extensions of said sheet, said depressed areas being deeper in the portion of said sheet overlaid by said insert than said depressed areas in said side extensions of said sheet;
    folding said side extensions of said sheet onto the second major surface of said insert to form said absorbent body.

2. A method of claim 1 wherein a relatively wide elongated material is first slit to form said elongated sheet and said insert.

3. The method of claim 1 wherein said pattern of depressed area is imposed by the action of water and pressure.

4. The method of claim 1 wherein said depressed areas are imposed by the action of heat and pressure.

* * * * *